(12) United States Patent
Zahniser et al.

(10) Patent No.: US 9,690,976 B2
(45) Date of Patent: Jun. 27, 2017

(54) IMAGING BLOOD CELLS

(71) Applicant: Roche Diagnostics Hematology, Inc., Westborough, MA (US)

(72) Inventors: Michael Zahniser, Jamaica Plain, MA (US); Kam Lin Wong, Bedford, MA (US); David Zahniser, Wellesley, MA (US); Robert Hohlfeld, Attleboro, MA (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 0 days.

(21) Appl. No.: 14/775,381

(22) PCT Filed: Mar. 11, 2014

(86) PCT No.: PCT/US2014/023401
§ 371 (c)(1),
(2) Date: Sep. 11, 2015

(87) PCT Pub. No.: WO2014/164757
PCT Pub. Date: Oct. 9, 2014

(65) Prior Publication Data
US 2016/0026852 A1    Jan. 28, 2016

Related U.S. Application Data

(60) Provisional application No. 61/776,740, filed on Mar. 11, 2013, provisional application No. 61/794,946, filed on Mar. 15, 2013.

(51) Int. Cl.
*G06K 9/00* (2006.01)
*G02B 21/36* (2006.01)
(Continued)

(52) U.S. Cl.
CPC ..... *G06K 9/00147* (2013.01); *G01N 15/1475* (2013.01); *G02B 21/367* (2013.01);
(Continued)

(58) Field of Classification Search
USPC ........ 382/100, 103, 106–107, 128–134, 162, 382/168, 173, 181, 189, 199, 209, 224,
(Continued)

(56) References Cited

U.S. PATENT DOCUMENTS 7,634,126 B2 * 12/2009 Ortyn .................... G01J 3/2889
356/326
2009/0203588 A1 * 8/2009 Willman .............. C12Q 1/6886
514/1.1
(Continued)

FOREIGN PATENT DOCUMENTS

WO        98/52018        11/1998

OTHER PUBLICATIONS

International Search Report and Written Opinion mailed Sep. 22, 2014 in international application No. PCT/US2014/023401, 17 pgs.

*Primary Examiner* — Seyed Azarian
(74) *Attorney, Agent, or Firm* — Fish & Richardson P.C.

(57) ABSTRACT

This document describes methods, systems and computer program products directed to imaging blood cells. The subject matter described in this document can be embodied in a method of classifying white blood cells (WBCs) in a biological sample on a substrate. The method includes acquiring, by an image acquisition device, a plurality of images of a first location on the substrate, and classifying, by a processor, objects in the plurality of images into WBC classification groups. The method also includes identifying, by a processor, objects from at least some classification
(Continued)

groups, as unclassified objects, and displaying, on a user interface, the unclassified objects and at least some of the classified objects.

27 Claims, 8 Drawing Sheets

(51) Int. Cl.
*G01N 15/14* (2006.01)
*G06K 9/48* (2006.01)
*G06K 9/62* (2006.01)
*G06T 7/00* (2017.01)
*G06T 7/11* (2017.01)
*G06T 7/136* (2017.01)
*G01N 33/574* (2006.01)
*G01N 15/00* (2006.01)

(52) U.S. Cl.
CPC ....... *G06K 9/0014* (2013.01); *G06K 9/00134* (2013.01); *G06K 9/481* (2013.01); *G06K 9/6278* (2013.01); *G06T 7/0012* (2013.01); *G06T 7/11* (2017.01); *G06T 7/136* (2017.01); *G01N 2015/008* (2013.01); *G06T 2207/10016* (2013.01); *G06T 2207/10024* (2013.01); *G06T 2207/10056* (2013.01); *G06T 2207/20016* (2013.01); *G06T 2207/30024* (2013.01); *G06T 2207/30242* (2013.01)

(58) Field of Classification Search
USPC ....... 382/232, 254–255, 274, 276, 286, 291, 382/305, 312; 356/326; 435/40.5, 7.23; 514/1.1; 348/79
See application file for complete search history.

(56) References Cited

U.S. PATENT DOCUMENTS

| | | | |
|---|---|---|---|
| 2011/0242308 A1* | 10/2011 | Igarashi | G01N 21/6458 348/79 |
| 2012/0262703 A1 | 10/2012 | Zahniser | |
| 2012/0263369 A1 | 10/2012 | Xie et al. | |
| 2012/0276555 A1* | 11/2012 | Kuhn | G01N 33/5076 435/7.23 |
| 2012/0322099 A1* | 12/2012 | Lapen | G01N 1/30 435/40.5 |

* cited by examiner

IMAGING BLOOD CELLS

CLAIM OF PRIORITY

This application is a U.S. National Phase Application under 35 U.S.C. 371 of International Patent Application No. PCT/US2014/023401, filed on Mar. 11, 2014, which claims the benefit of U.S. provisional application 61/776,740, filed on Mar. 11, 2013, and U.S. provisional application 61/794,946, filed Mar. 15, 2013. The entire contents of these applications are hereby incorporated by reference.

TECHNICAL FIELD

The invention relates to imaging blood cells, e.g., using electronic imaging systems.

BACKGROUND

Many imaging and scanning applications acquire images in an automated fashion. Interpreting such images may require identifying one or more objects within the images. While such identification may be performed manually, the process is time consuming and may be prone to errors.

SUMMARY

Biological specimens can be imaged at multiple individual wavelengths and a set of images can be acquired. Characteristics of the biological specimens can be determined by processing one or more of the images. For instance, processing of low-magnification images can include counting of red blood cells (RBCs), locating and counting blood constituents (e.g., white blood cells (WBCs) and nucleated red blood cells (nRBCs)), and counting platelets. For instance, processing of high-magnification images can include characterizing features of RBCs, calculating a WBC differential, and classifying WBCs.

In one aspect, a method for locating cells in a biological sample on a substrate includes acquiring, by an image acquisition device, a plurality of images of a first location on the substrate. Each image of the plurality of images is acquired at a different illumination wavelength. The method also includes identifying, by a processor, locations of cytoplasmic material in the plurality of images, and identifying, by a processor, locations of cell nuclei in the plurality of images. The method further includes identifying, by a processor, locations of cells in the plurality of images based on the locations of cytoplasmic material and the locations of cell nuclei. The method also includes assigning, by a processor, cell types to at least some of the cells in the plurality of images, and counting at least one cell type in the plurality of images.

In another aspect, the disclosure features a method of determining a white blood cell (WBC) differential of a biological sample on a substrate. The method includes acquiring, by an image acquisition device, a plurality of images of a first location on the substrate, including acquiring each image of the plurality of images at a different illumination wavelength, and identifying, by a processor, locations of WBC nuclei in the plurality of images. Identifying the locations of WBC includes generating a first nuclear mask based on a first assumption about the WBCs in the plurality of images, generating a second nuclear mask based on a second assumption about the WBCs in the plurality of images, and intersecting the first nuclear mask and the second nuclear mask to generate a nuclear segmentation. The method also includes measuring one or more features of the WBCs based on the nuclear segmentation, and using the measured features to determine the WBC differential.

In another aspect, the disclosure features a method of classifying white blood cells (WBCs) in a biological sample on a substrate. The method includes acquiring, by an image acquisition device, a plurality of images of a first location on the substrate, and classifying, by a processor, objects in the plurality of images into WBC classification groups. The method also includes identifying, by a processor, objects from at least some classification groups, as unclassified objects, and displaying, on a user interface, the unclassified objects and at least some of the classified objects.

In other aspects the disclosure features computer readable storage devices that are encoded with computer readable instructions that cause one or more processors implement the methods outlined above. In further aspects, the disclosure features an imaging system that includes an image acquisition device configured to acquire a plurality of images of a first location on a substrate. Each image of the plurality of images can be acquired at a different illumination wavelength. The systems also include one or more processors, connected to the image acquisition device, wherein the processor is configured to implement the methods outlined above.

Implementations of the above aspects can include one or more of the following.

The plurality of images can be acquired using a 10× objective lens. The at least one cell type can include at least one of white blood cells and nucleated red blood cells. Acquiring the plurality of images can include acquiring the plurality of images using a 50× objective lens. The first assumption can include an assumption that the WBCs are granulocytes. The second assumption can include an assumption that the WBCs are agranular. The features can include one or more of an area of a WBC, a shape of a WBC, a color of a WBC, and optical density of a WBC, and a texture of a WBC. At least one of a value for a nuclear complexity of neutrophils and a value for an atypicality of lymphocytes can be determined in the WBC classification groups. At least one of the value for the nuclear complexity and the value for the atypicality can be displayed on the user interface. Non-WBC objects can be removed from the images prior to classifying the objects. The non-WBC objects can include one or more of platelets, clumps, giant platelets, and micromegakaryocytes. The objects in the plurality of images can be classified using a multi-stage classifier. At least one stage of the multi-stage classifier can include a linear discriminant analysis (LDA) based classifier. At least another stage of the multi-stage classifier can include a Bayesian classifier. The WBC classification groups can be based on WBC maturation pathways. The unclassified objects can include one or more of immature cells, blasts, promonos, and prolymphs. Rare, damaged, or out-of-focus cells can be excluded from being classified into the WBC classification groups.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Biological specimens can be imaged at multiple individual wavelengths and a set of images can be acquired. Characteristics of the biological specimens can be determined by processing one or more of the images. For instance, processing of low-magnification images can include counting of red blood cells (RBCs), locating and counting blood constituents (e.g., white blood cells (WBCs) and nucleated red blood cells (nRBCs)), and counting platelets. For instance, processing of high-magnification images can include characterizing features of RBCs, calculating a WBC differential, and classifying WBCs. Calculating a WBC differential can include, for example, counting a number of different types of WBCs in the blood. In some implementations, calculating a WBC differential can include calculating percentages of different types of WBC in the blood.

Imaging Systems

Figure 1:
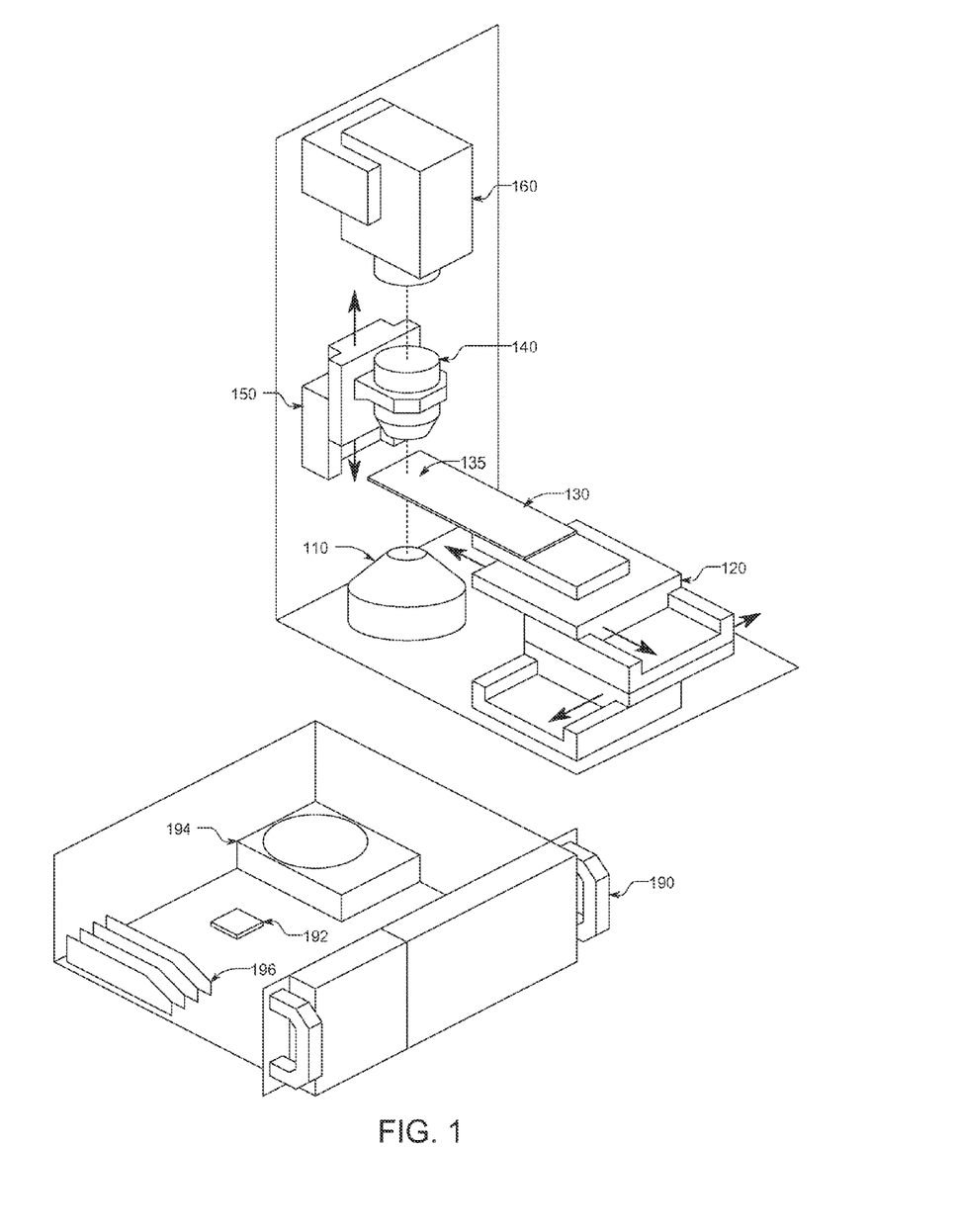
FIG. 1 is a schematic diagram of an embodiment of an imaging system.

FIG. 1 shows one embodiment of an imaging system 100 that employs the fast auto-focusing methods described herein. Imaging system 100 includes imaging hardware 105 that is controlled by a computer 190. The computer 190 generally includes a central processing unit 192, a hard drive 194, and random access memory 196.

In the imaging system shown in FIG. 1, a light source 110 illuminates a slide 130 comprising a biological specimen 135. The light source 110 includes individual light sources of different colors. In one example, the light source 110 may include blue, green, yellow, and red light emitting diodes (LEDs). Other types of colored light sources can also be used. The light source 110 can be used for low magnification imaging, high magnification imaging, or both.

The slide is mounted on a first motorized stage 120 capable of moving in a horizontal plane (parallel to the surface of the slide that is imaged) such that any part of the slide 130 can be positioned under an objective lens 140. A second motorized stage 150 moves the objective lens 140 up and down to facilitate focusing on the specimen 135 deposited on slide 130. The distance between the slide 130 and the objective lens 140 is referred to as the "focal distance." A reduction in focal distance implies, in this example, moving the objective lens 140 vertically towards the slide 130.

Alternatively, the focal distance can also be adjusted by moving the slide 130 (for example by moving the first motorized stage 120) vertically towards the objective lens 140. In some implementations, both the slide 130 and the objective lens 140 can move to facilitate adjusting the focal distance. The axes, with respect to which the first motorized stage 120 is moved in a horizontal plane, are typically referred to at the X and Y axes. The vertical axis along which the second motorized stage 150 moves the objective lens 140 is typically referred to as the Z axis. The three axes define a coordinate system that the system 100 utilizes to image any (x, y, z) point in space relative to the slide 130.

Light from the source 110 passes through the slide 130 and is projected by the objective lens 140 onto the sensor of the camera 160. The sensor may, for example, be a charge-coupled device (CCD) array. FIG. 1 depicts an example of "bright field" microscopy where objects on the slide are visible because they absorb light and are therefore darker in the image produced by the camera. The imaging hardware 105 can include one or more additional lenses. Other microscopic modes such as fluorescence, dark-field, or phase contrast can also generate images to which the fast auto-focus methods described herein can be applied.

If an image is acquired at a non-optimal focal distance, the image is blurry and typically unsuitable for many image processing applications. If the surface of the slide 130 were perfectly planar, the system 100 could acquire in-focus images simply by determining the proper z height corresponding to an in-focus image at three (x, y) locations and then fitting a plane to those (x, y, z) points. The plane equation would then provide an in-focus z height for any other (x, y) location on the slide. In practice, however, the focal distance for a given location may not be accurately determined from a plane fit as described above due to irregularities in the surface of the slide 130 and/or the stage 120. Therefore, in general, the focal distance may need to be adjusted slightly for each image that is acquired at a different (x, y) location on the slide.

After image acquisition, camera 160 sends images to the computer 190 for processing. If the images are processed quickly enough, focal distance data from one image location may be used to adjust the focal distance at the next location for capturing an image. This allows the system to adjust to variations in focal distances corresponding to different locations and, in turn, produce more accurately focused images for display. For example, if one region of the slide 130 is slightly thicker than others and ten locations are imaged within that region, the change in thickness can be discovered after the first image is acquired and additional images taken at other locations within the region can be acquired at slightly adjusted focal distances to compensate for the change in thickness using the methods described herein.

In some examples, low magnification images can be acquired with a 10× objective, a 0.5× optical coupler, and a 2 megapixel CCD camera. In some examples, high magnification images can be acquired with a 50× objective, a 1× optical coupler, and a 0.3 megapixel, 200 frames per second camera.

In some examples, a set of black and white images (referred to herein as a "stack" of images) is acquired of the slide at an imaging location. Each image of the set acquired using a single wavelength of light (e.g., using each of the blue, green, yellow, and red LEDs of the light source 110). If desired, color images, such as color JPEG images, can be created from the set of black and white images for display purposes. In some examples, objective lenses are not corrected for oil immersion or for the presence of a coverslip.

Each image of the set is background corrected and aligned with each other image of the set. If more than one image is taken with a certain color at a particular location, one of those images is selected (e.g., the image with the best focus). An on-the-fly estimate of the focal plane of the slide can be updated during image acquisition. The set of images is processed by one or more imaging modules to yield measurements that can be used to determine blood count, white blood cell (WBC) differential, and other characteristics of the biological specimen.

Illuminating a specimen with different colors of light can result in different information being extracted from the acquired images. For example, in the case of imaging a specimen containing blood cells, cells may appear differently under different colored illumination, thereby facilitating easier identification, classification, or differentiation. For example, red blood cells absorb significant amounts of blue light due to the presence of hemoglobin, and cell nuclei stained with standard Romanowsky stains absorb yellow light.

Figure 2:
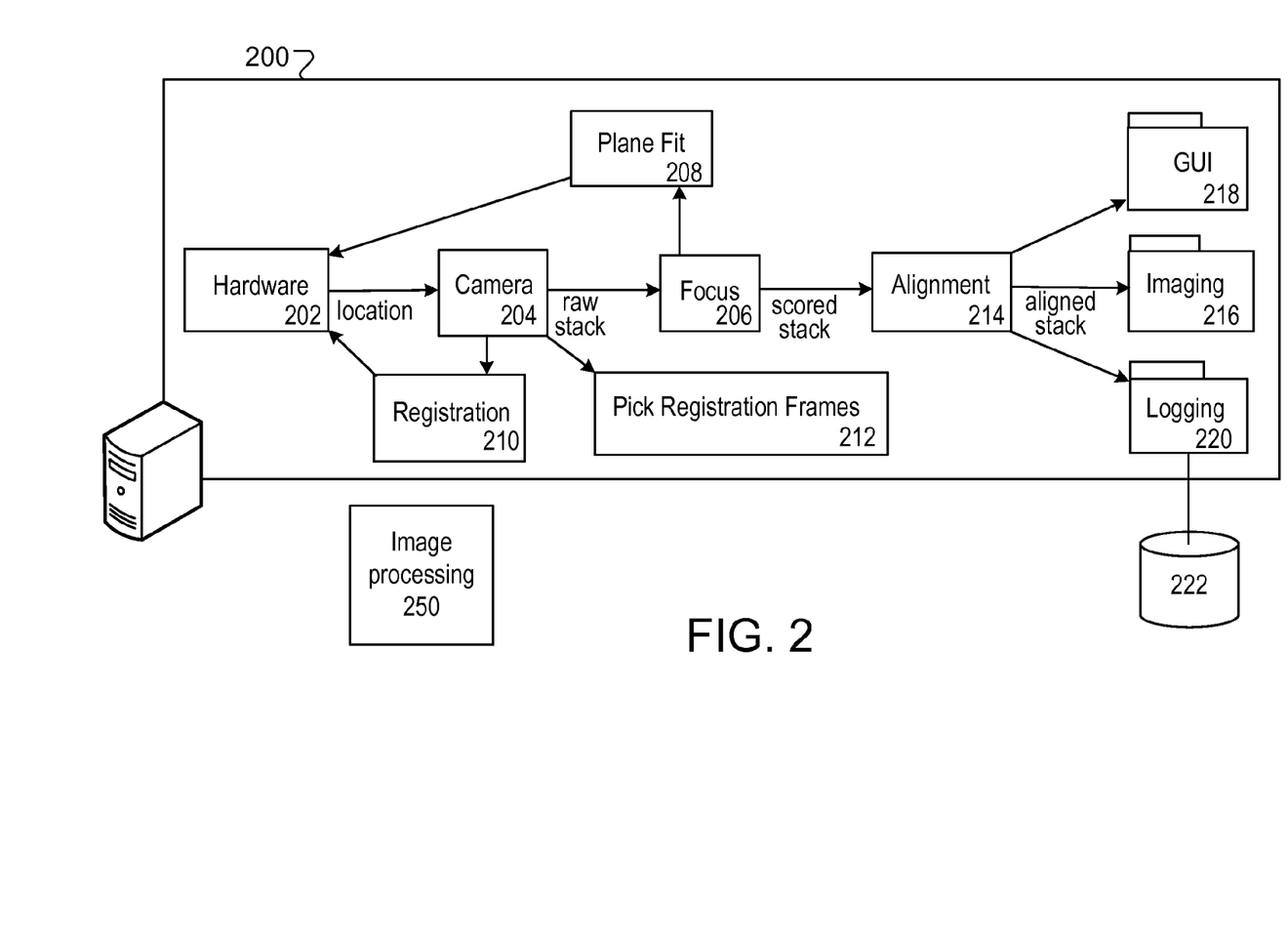
FIG. 2 is a block diagram showing various modules of an imaging system.

Referring to FIG. 2, image acquisition and processing is controlled by a control system 200. In the depicted example, the control system 200 is implemented by a single computer 201. In some examples, the control system 200 can be implemented by multiple computers. For instance, some modules of the control system 200 can be implemented by a first computer and other modules of the control system 200 can be implemented by a second computer.

A hardware module 202 sends commands to imaging hardware (e.g., controlled by an imaging module 216), which in turn sends pulses to the camera 160 to trigger image acquisition. The acquired images are transferred to a computer (e.g., the computer 201). A camera module 204 packages the acquired images into stacks.

While a slide is being imaged, a focus module 206 examines each stack of images and estimates at what height the stack is likely to have been acquired, e.g., based on the relative focus scores of the images of the stack. The focus module 206 reports these height estimates to a plane fit module 208. Before each location is imaged, the hardware module 202 asks the plane fit module 208 for a focal plane estimate at that location. This mechanism of updating the focal plane estimate with image acquisition can be used by the imaging system 100 or the imaging module 216 or both to adapt to irregularities on the surface of a slide. In some instances, there may be a lag in the adaptive response to slide irregularities, e.g., due to pipelining of the focal plane estimates.

A registration module 210 and a pick registration frames module 212 can be used to match coordinate systems between low magnification images and high magnification images. Thus, for instance, any object found during low magnification imaging can be precisely located and imaged during high magnification imaging.

An alignment module 214 provides a capability to align images of a stack. In some instances, the raw images of a stack do not align with each other, for instance, due to slide movement, slightly off-center LED dies, optical effects of the lens, or other factors. Furthermore, under low magnification, images acquired under different illumination colors may each have a slightly different magnification if the lens is not perfectly color-corrected. Under high magnification, the scale of the four colors may be the same but the images may still be misaligned. In one example, to align low magnification images, an algorithm can be used that selects a set of high-contrast tie points (e.g., cells) in a target image, locates the same tie points (e.g., cells) in a second image, and transforms the second image to align the second image with the target image. In one example, to align high magnification images, an algorithm can try all offsets within a limited range of pixels and select the offset for each color that maximizes the $R^2$ correlation with the image of a target color (e.g., with a green image).

Images, results of analysis of the images, or both can be displayed on a user interface, such as a graphical user interface (GUI) 218. Images, results of analysis of the images, or both can be logged by a logging module 220 and stored in a file, database 222, or other storage location.

In some examples, a calibration can be performed when the imaging system 100 is initialized, e.g., with no slide in place. Calibration can include blank image acquisition and initial shutter adjustment. In some examples, for each slide, a focus search can be performed to determine a tilt of the slide, e.g., using a fast adjustment algorithm that takes only a fraction of a second.

Image Processing

Various types of image processing can be performed on stacks of images acquired using the imaging system 100. For instance, processing of low-magnification images can include counting of red blood cells (RBCs), locating and counting blood constituents (e.g., white blood cells (WBCs) and nucleated red blood cells (nRBCs)), counting platelets, and other types of processing. For instance, processing of high-magnification images can include characterizing features of RBCs, calculating a WBC differential, classifying WBCs, and other types of processing.

Referring again to FIG. 2, in some examples, image processing is executed by an image processing module 250 that is implemented by the computer 201 implementing the control system 200. In some examples, the image processing module 250 is implemented by a different computer that does not implement any module of the control system 200.

Processing of Low Magnification Images

In one example, low magnification images can be processed to count RBCs. RBCs can have various sizes (e.g., RBCs can be large, small, or fragmented). RBCs can also have various appearances (e.g., RBCs can have large or small pallor or unusual shapes). To account for these variations, a filter (referred to herein as a "spot filter") is applied that transforms each RBC, regardless of its size or pallor, into a smaller, dark spot. The transformed spots can be easier to count than images of original, varied RBCs. In some instances, the spot filter can be applied only to the blue image of a stack of images, because white cells are nearly invisible in blue images. The filtered images can be processed to count the RBCs, including masking dust, debris, and other contaminants; smoothing the image; determining an average area of a RBC, counting the spots in the image; rejecting artifacts (e.g., stain debris); and adjusting the count based on the "dust area."

Figure 3:
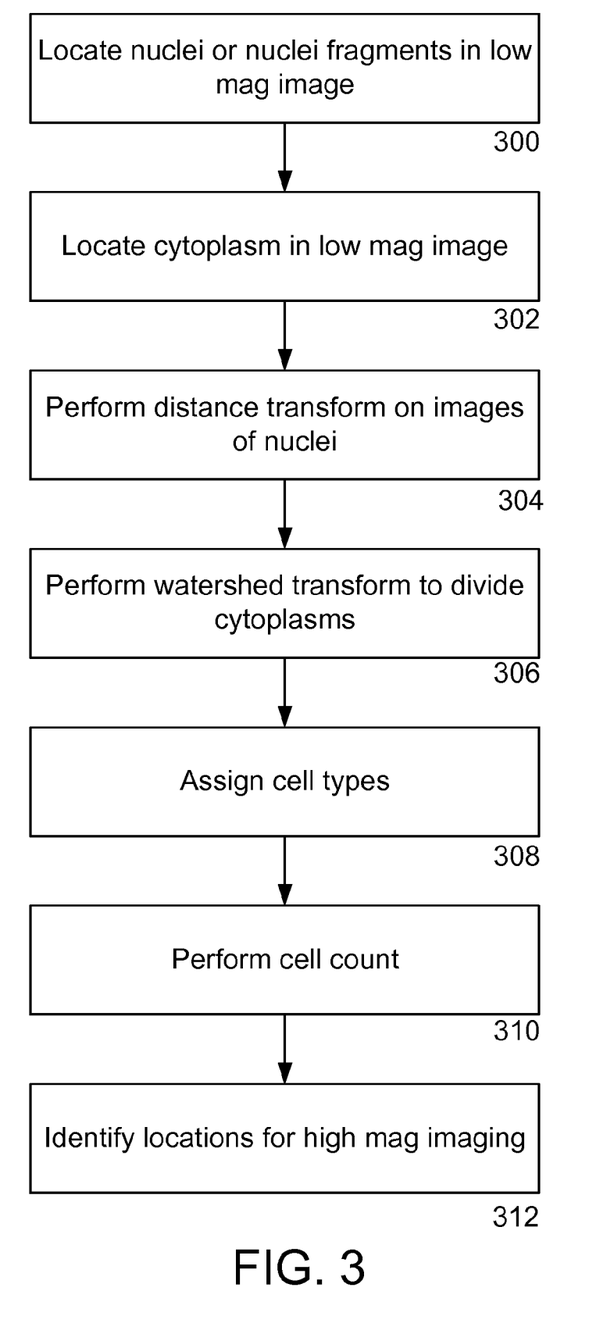
FIG. 3 is a flow chart of a process for locating and counting white blood cells (WBCs) and nucleated red blood cells.

In one example, low magnification images can be processed to locate WBCs and nRBCs. WBCs can be located during low magnification imaging, and in some examples can be revisited during high magnification imaging. Referring to FIG. 3, a low magnification image is processed by locating blue spots of approximately the right size to be a nucleus or nuclear fragment (300). Regions of the image that are the right color to be cytoplasm are located (302). A distance transform is performed on the nucleus images, constrained to within the cytoplasm boundaries (304). A watershed transform with a size limit is performed (306) to divide touching cytoplasms. Cell types can then be assigned (308), e.g., using a ten part classifier that identifies five normal WBC types, platelets, nRBCs, double WBCs, damaged WBCs, and artifacts (e.g., stain debris). Once the classification has been performed, a cell count is performed (310) and locations of interest for high magnification can be selected (312).

In one example, low magnification images can be processed to count platelets. Platelets can be located and counted using the filter counting approach described above for RBCs, but applying the spot filter to the yellow and blue images and skipping areas that are under objects already identified as WBCs. A classifier can be used to differentiate platelets from artifacts to determine the final count of platelets.

Processing of High Magnification Images

High magnification imaging provides the ability to examine cells more closely than in low magnification imaging. In some examples, a high magnification of a WBC can be used to classify the WBC. In some examples, a high magnification image of RBCs or platelets can be used to characterize the RBCs or platelets.

In one example, high magnification images can be processed to characterize features of RBCs, such as mean cell volume (MCV), hemoglobin content (MCH), reticulocyte percent, or other features, such as other elements of a complete blood count (CBC). For these characterizations, a large number of RBCs can be imaged under high magnification (e.g., at least about 10,000 RBCs). Under the assumption that RBC aggregation is random, high magnification images of single, non-overlapping RBCs can be selected for measurement.

MCV and MCH can be calculated from a weighted sum of nine features: the area of a RBC, an integrated optical density of the RBC for each of the four imaging colors, and a volume measurement of the RBC for each of the four imaging colors. The reticulocyte percentage can be determined by analyzing the level of blue content within each of the imaged RBCs. Other elements of a CBC can be determined from the RBC count (determined from low magnification imaging, e.g., as described above), the MCH, and the MCV of a sample.

Additional features of high magnification images of RBCs can be used to determine the potential presence of inclusions in the RBCs, to assess RBC shapes, or to perform other characterizations of the RBCs. Specific RBCs with potential inclusions, unusual shapes, or both, can be tagged for presentation to a user. For instance, RBCs with potential inclusions can be displayed in an RBC gallery. For instance, RBCs with unusual shapes can be assigned values corresponding to their shapes, allowing the RBCs in the gallery to be sorted by shape.

In one example, high magnification images can be processed to determine a WBC differential. An accurate WBC differential can be determined based on segmentation for WBC nuclei and for the cytoplasm. WBC nuclei generally stain the same color or similar colors and thus can be relatively easy to recognize. Cytoplasm can stain many different colors, and in some cases can be almost transparent. In addition, WBCs often aggregate; to obtain an accurate WBC differential, the WBCs in an aggregate can be counted individually.

Figure 4:
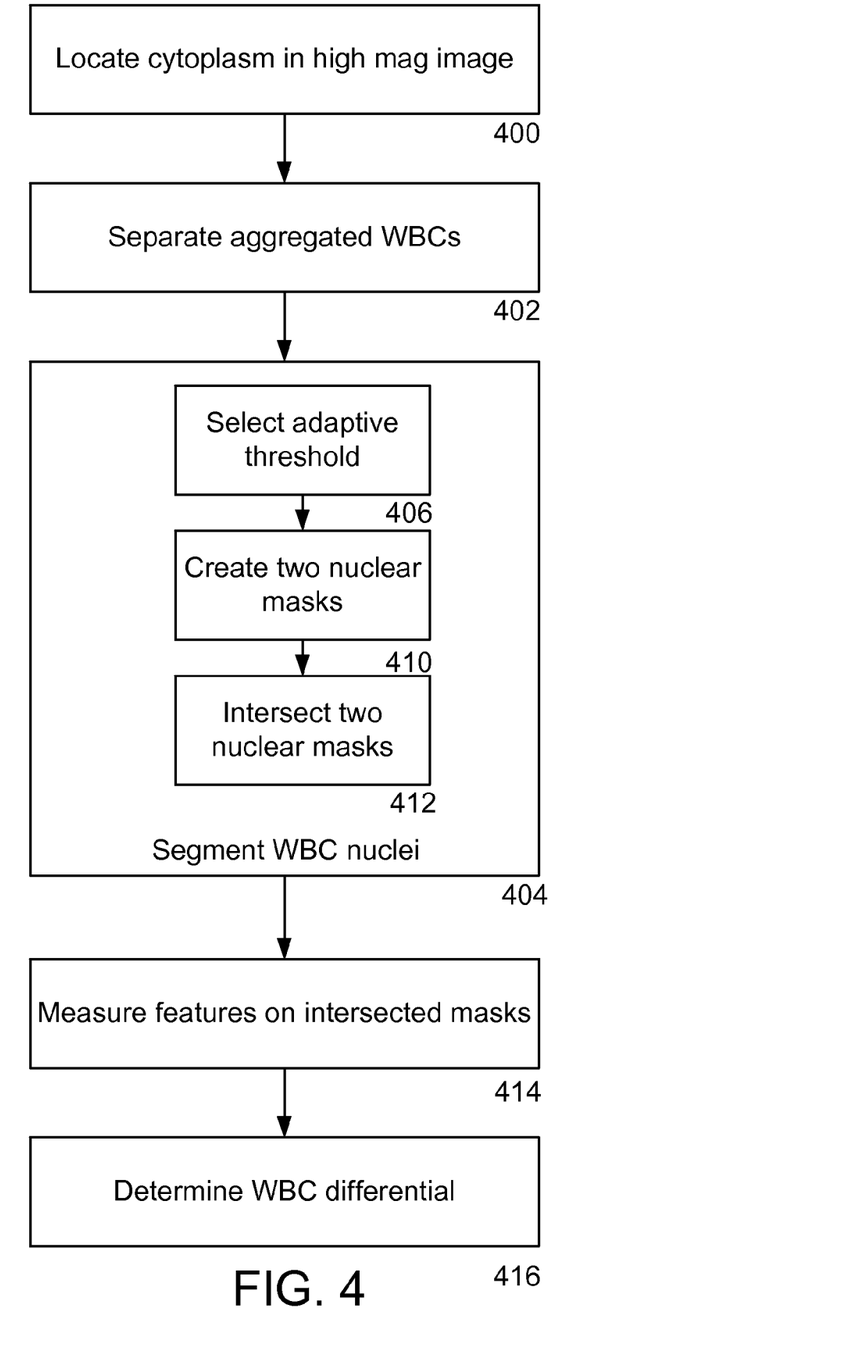
FIG. 4 is a flow chart of a process for determining a WBC differential.

Referring to FIG. 4, to process high magnification images to determine a WBC differential, the cytoplasmic material is located (400). Aggregated WBCs are separated (402). The nuclei of the WBCs are segmented (404). To account for any variations in the stained color of the WBC nuclei, an adaptive threshold can be chosen (406) within each cytoplasm mask based on the yellow, green, and blue images. Two nuclear masks are created (410), one mask of the nucleus segmented as if it were a granulocyte and the other mask of the nucleus segmented as if it were agranular. The two nuclear masks are intersected (412) to produce a nuclear segmentation that is well suited to both granulocytes and agranular nuclei.

Features (e.g., over 400 features) are measured on the intersected cell masks (414). Some features can be measured only on the cytoplasm or only on the nucleus region of a WBC; other features can be measured on the entire cell. Area and shape features can be determined based upon just the nuclear and cytoplasmic masks. Color features can be determined based on the grey levels of individual pixels within the nuclear or cytoplasmic mask in different color images. Optical density and texture features can be determined based on the four different color images, within the nuclear or cytoplasmic masks. The measured features can be used to determine the WBC differential (416).

In one example, high magnification images can be processed to classify WBCs. A multi-stage "tree" classifier can be used. The classifier can have mostly linear discriminants (LDA). The classifier can also include a few non-LDA nodes, e.g., where the non-LDA nodes can be helpful for separating populations without a normal distribution. In some implementations, at least one of the non-LDA nodes can implement a Bayesian classification system.

Figure 5:
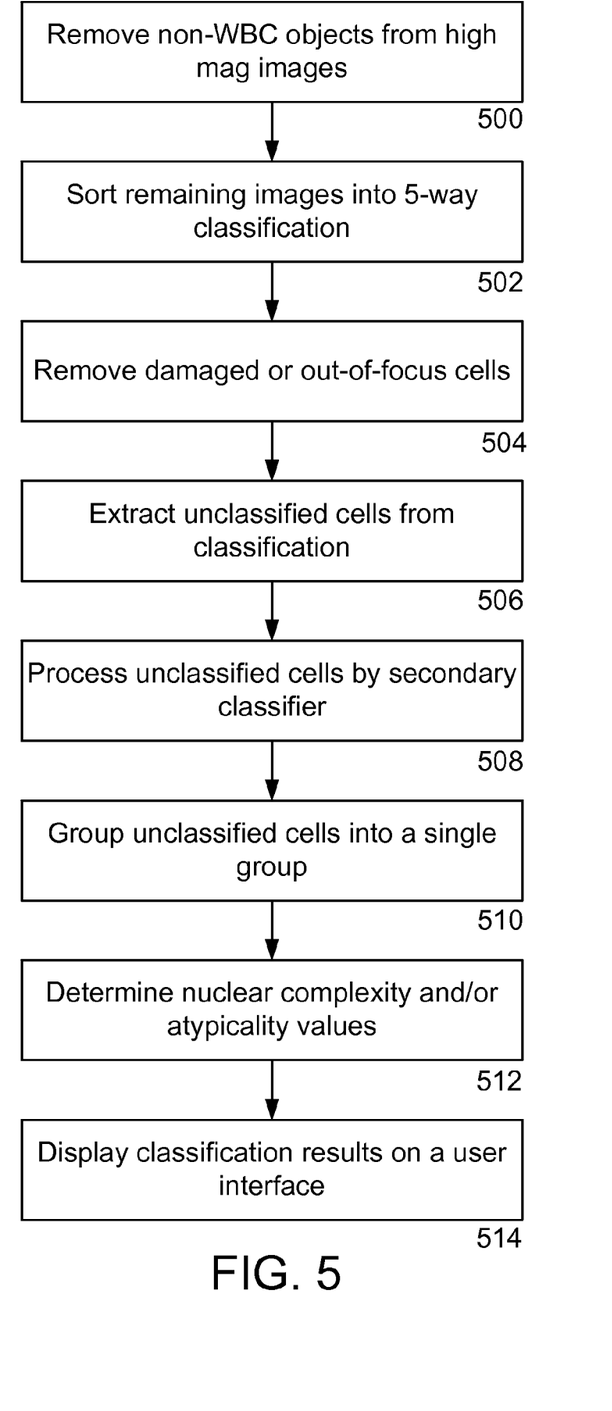
FIG. 5 is a flow chart of a process for classifying WBCs.

Referring to FIG. 5, the classifier sorts out any non-WBC objects in the images that may be similar to WBCs, such as clumps of platelets, giant platelets, micromegakaryocytes, or other non-WBC objects (500). The remaining objects are sorted into a rough five-way classification (502), e.g., along the biological lines of WBC maturation pathways. Any damaged or out-of-focus cells from the fringes of each sorted group are removed from the classification (504). Each of the five groups is processed to extract potential unclassified cells, such as immature cells, blasts, promonos, prolymphs, or other unclassified cells, and to correct mistakes in the classification of the normal types (506). In some examples, the classification scheme can be designed to minimize the number of false positive unclassified cells. For instance, each of the groups of unclassified cells (e.g., immature granulocytes, blasts, promonos, prolymphs) that were extracted is processed by a secondary classifier (508) to check for false positives. The cells that remain unclassified are grouped together into a single group (510).

A value indicating the "nuclear complexity" of neutrophils can be determined. A value indicating the "atypicality" of lymphocytes can also be determined (512).

The results of the classification can be displayed on a viewing station (514), such as a user interface of a computing device. In some examples, the group of unclassified cells can be displayed on the top line of a WBC tab on the user interface. In some examples, the unclassified cells can be displayed, e.g., on a front page of a WBC gallery, along with the equivalent of a hundred cell differential by choosing hundred cells at random from the normal WBC classification categories. Additional WBCs can be displayed responsive to instructions from a user. The nuclear complexity and atypicality values can also be displayed or made available to the user. For instance, a user can classify neutrophils as "banded" or "segmented" based on their nuclear complexity value and can sort neutrophils as banded or segmented based on this classification. A user can also classify lymphocytes as "atypical" based on their atypicality value and can sort lymphocytes as typical or atypical based on this classification.

Cell Classification

A multi-stage classifier can be used to classify cells, such as white blood cells (WBCs), and other objects, according to one or more features extracted from images of the biological sample. The multi-stage classifier can perform multiple stages of classification. In some implementations, different types of classifiers are used at the different stages. For example, one stage of the classifier can use a linear discriminant analysis (LDA) based classifier and another stage can use a non-LDA classifier, such as a Bayesian classifier.

In general, the multi-stage classifier can have a complex topology that can combine topologies from two or more other classifiers, such as tree classifiers and ladder classifiers, to enable efficient, accurate classification of WBCs, or blood cells in general.

The classifier may classify objects into cell types, such as lymphocytes, monocytes, neutrophils, basophils, and eosinophils. The classifier may classify objects into specific other types of objects, such as various specific types of immature cells, or may classify these types of objects into a general category (e.g., an unclassified category).

Each stage of the multi-stage classifier can classify objects into a plurality of classifications. In some instances, the classification of an object at a particular stage may confirm the classification of the object from an earlier stage (for instance, a lymphocyte may remain classified as a lymphocyte). In some instances, the classification of an object at a particular stage may reclassify the object into another category into which the object had not been classified during an earlier stage (for instance, in a first stage, the object may have been classified as a lymphocyte rather than a neutrophil; in a second stage, the object may be reclassified as a neutrophil). In some instances, the classification of an object at a particular stage may classify the object into a category that was not available at an earlier stage (for instance, a lymphocyte may be classified as a blastocyst, which was not available for classification in earlier stages).

Objects can be classified based on feature vectors representing one or more features of the objects, such as cell area, cell shape, cell color, cell optical density, cell texture, and other features of the cells. In some examples, the feature vector used for classification can be substantially same for each stage of classification. In some examples, a different feature vector can be used for some or all stages of classification. For instance, feature vectors for later classification stages may have more features than feature vectors for earlier classification stages, enabling more accurate classification, or classification into a different set of classes.

Figure 6:
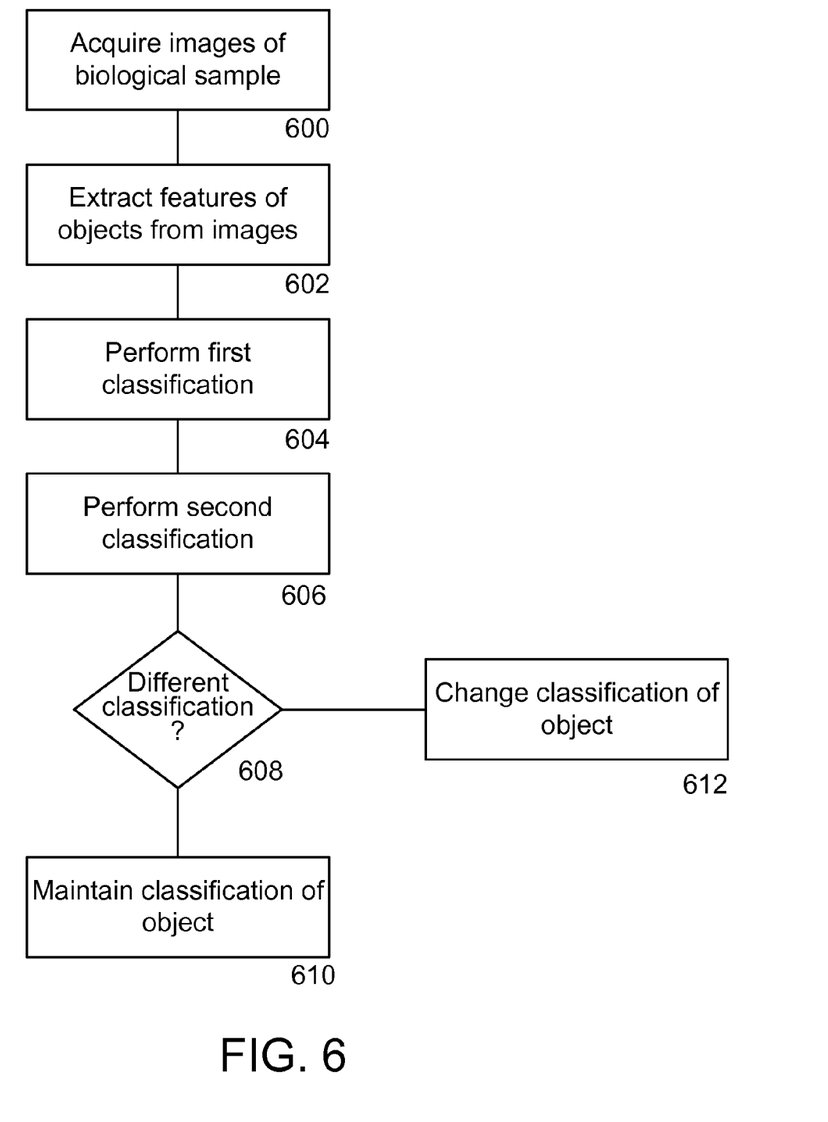
FIG. 6 is a flow chart of a process for classifying cells.

Referring to FIG. 6, in a general approach to multi-stage classification of objects in a biological sample, one or more images of a substrate on which the biological sample is disposed are acquired (600). A plurality of features of the objects is extracted from the one or more images (602), e.g., using one or more of the techniques described above.

Multiple classifications are performed for each object. For instance, a first classification is performed (604) and a second classification is performed (606). Each classification is based on a corresponding feature vector composed of one or more of the extracted features of the respective object. If the results of the second classification are the same as the results of the first classification (608), the classification of the object is maintained (610). If the results of the second classification differ from the results of the first classification (608), the classification of the object is changed (612). For instance, changing a previous classification of the object can include reclassifying the object into a category that was available during a previous classification. Changing a previous classification can include classifying the object into a category that was not available during a previous classification.

Any number of classifications can be performed.

Figure 7:
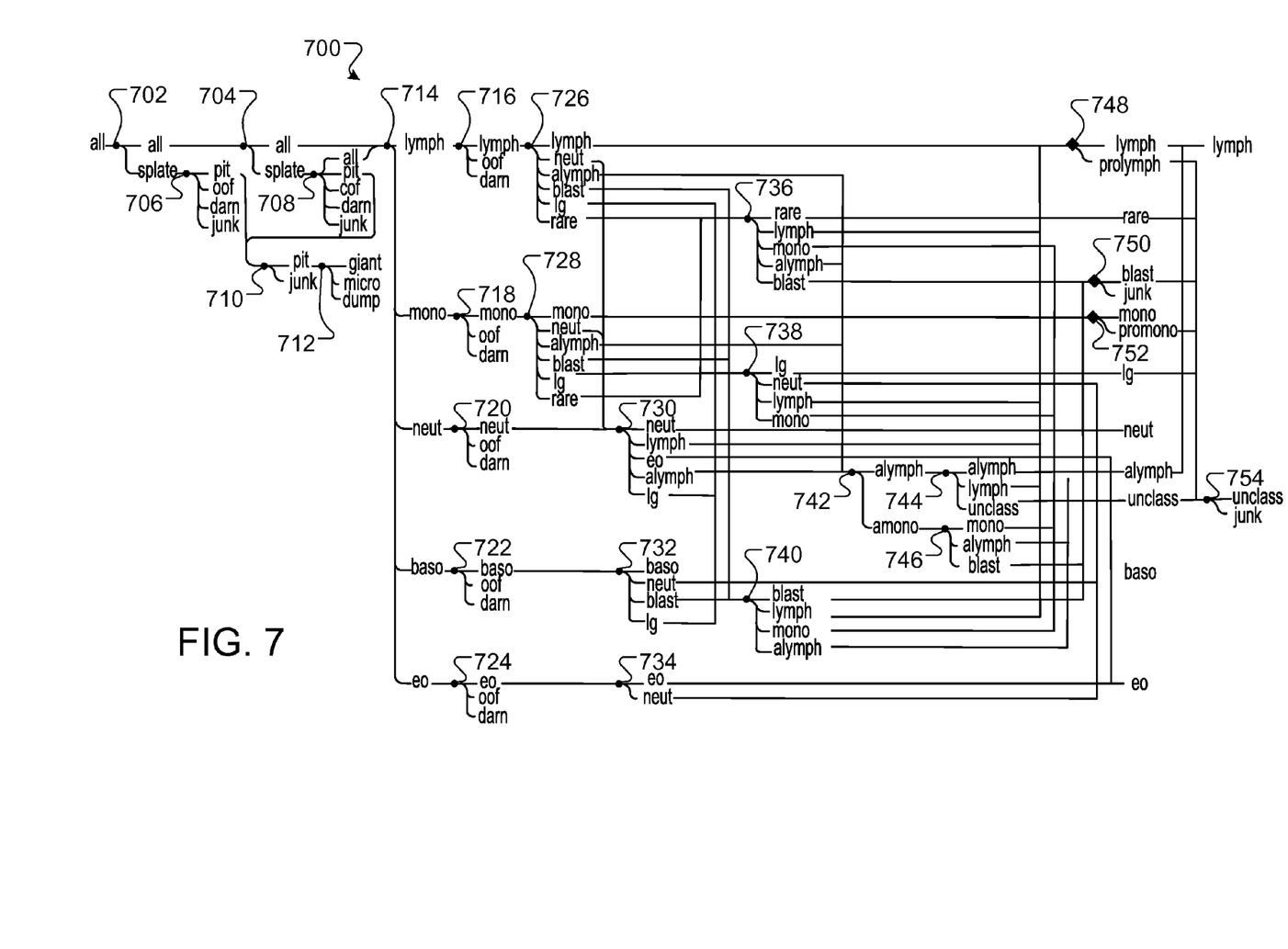
FIG. 7 is an example classification scheme.
Figure 8:
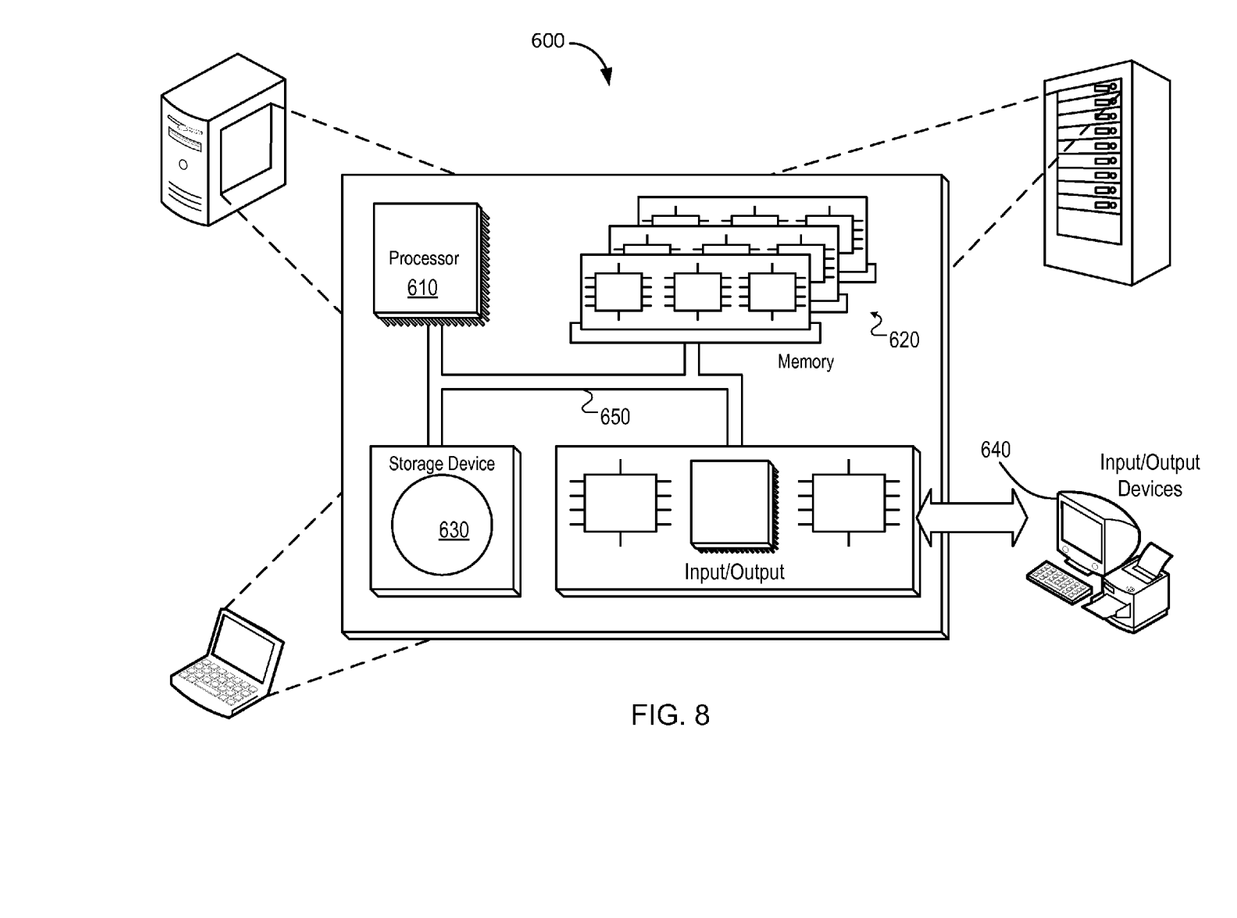
FIG. 8 is a schematic diagram of a computing device.

Referring to FIG. 7, an example topology of a multi-stage classifier 700 is depicted. The classifier depicted in this example classifies objects in multiple stages according to an LDA classification (depicted by circular nodes such as node 702) and non-LDA (e.g., Bayesian) classification (depicted by diamond nodes such as node 748).

At a first classification node 702, f-platelets (referred to as "fplate") are removed from the set of "all" objects for classification. At a second classification node 704, s-platelets ("splate") are also removed from the set of "all" objects for classification.

The f-platelets can be classified into platelets (referred to as "plt"), out-of-focus ("oof") material, damaged ("dam") material, or junk (node 706). The s-platelets can be reclassified as "all" or classified into platelets, oof material, damaged material, or junk (node 708). The objects classified as platelets at nodes 706, 708 are further classified at nodes 710, 712. The objects reclassified as "all" are returned to the set of "all" objects for further classification.

The set of "all" objects can be further classified at node 714 into five cell types: lymphocytes ("lymph"), monocytes ("mono"), neutrophils ("neut"), basophils ("baso"), or eosinophils "(eo"). The objects in each of these classifications are classified to remove out-of-focus or damaged objects from the classification (nodes 716, 718, 720, 722, 724).

The objects in each cell type are further classified. Some classifications can result in the classification of an object being maintained (e.g., a lymphocyte may remain classified as a lymphocyte). Some classifications can result in an object being reclassified as a different cell type (e.g., a lymphocyte may be reclassified as a neutrophil). Some classifications can result in an object being classified into a new classification (e.g., a lymphocyte may be classified as a blastocyst). In the example shown, the following classifications can occur:

Lymphocytes (node 726) can remain classified as lymphocytes, can be reclassified as neutrophils, or can be classified as atypical lymphocytes ("alymph"), blastocysts ("blast"), immature granulocytes ("ig"), or rare cells ("rare).

Monocytes (node 728) can remain classified as monocytes, can be reclassified as neutrophils, or can be classified as atypical lymphocytes, blastocysts, immature granulocytes, or rare cells.

In subsequent classification stages, all objects in a particular classification are treated together, regardless of the nodes at which those objects were classified:

Neutrophils (node 730) can remain classified as neutrophils, can be reclassified as lymphocytes or eosinophils, or can be classified as atypical lymphocytes or immature granulocytes. Node 730 classifies objects that were classified as neutrophils by nodes 720, 726, and 728.

Basophils (node 732) can remain classified as basophils, can be reclassified as neutrophils, or can be classified as blastocysts or immature granulocytes.

Eosinophils (node 734) can remain classified as eosinophils or can be reclassified as neutrophils.

Further classification stages also treat all objects in a particular classification together, regardless of the nodes at which those objects were classified, as illustrated by the following examples:

Rare cells (node 736) can remain classified as rare cells or can be reclassified as lymphocytes, monocytes, alymphocytes, or blastocysts. Node 736 classifies objects that were classified as rare cells by nodes 726 and 728.

Immature granulocytes (node 738) can remain classified as immature granulocytes or can be reclassified as neutrophils, lymphocytes, or monocytes. Node 738 classifies objects that were classified as immature granulocytes by nodes 726, 728, 730, 732.

Blastocysts (node 740) can remain classified as blastocysts or can be reclassified as lymphocytes, monocytes, or atypical lymphocytes. Node 740 classifies objects that were classified as blastocysts by nodes 726, 728, 732.

Atypical lymphocytes (node 742) can remain classified as atypical lymphocytes or can be classified as atypical monocytes ("amono"). Node 742 classifies objects that were classified as atypical lymphocytes by nodes 726, 728, 730, 736.

Atypical lymphocytes (node 744) undergo a further classification and can remain classified as atypical lymphocytes, can be reclassified as lymphocytes, or can be designated as unclassified ("unclass"). Node 744 classifies objects that were classified as atypical lymphocytes by node 742.

Atypical monocytes (node 746) can be reclassified as monocytes, atypical lymphocytes, or blastocysts. Node 746 classifies objects that were classified as atypical monocytes by node 742.

Lymphocytes (node 748) can be classified by a non-LDA classifier, such as a Bayesian classifier, as lymphocytes or prolymphocytes ("prolymph"). Node 748 classifies objects that were classified as lymphocytes by nodes 726, 730, 736, 738, 740, 744.

Blastocysts (node 750) can be classified by a non-LDA classifier as blastocysts or junk. Node 750 classifies objects that were classified as blastocysts by nodes 736, 740, 746.

Monocytes (node 752) can be classified by a non-LDA classifier as monocytes or promonocytes ("promono"). Node 752 classifies objects that were classified as monocytes by nodes 728, 736, 738, 740, 746.

Node 754 classifies objects as either unclassified or junk. Node 754 classifies objects that were classified as prolymphocytes from node 748, rare cells from node 736, blastocysts from node 750, promonocytes from node 752, immature granulocytes from node 738, and unclassified objects from node 744.

The classifier results in the classification of objects as follows:

Lymphocytes (from nodes
Monocytes (from nodes)
Neutrophils (from nodes)
Basophils (from nodes)
Eosinophils (from nodes
Unclassified objects (from node 754)
Junk (from node 754)

This multi-stage classifier can provide a scheme that enables efficient and accurate classification of objects.

Overview of a Computing System

FIG. 6 is a schematic diagram of a computer system 600 that can be used to control the operations described in association with any of the computer-implemented methods described herein, according to one implementation. The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In some implementations, the memory 620 is a computer-readable medium. The memory 620 can include volatile memory and/or non-volatile memory.

The storage device 630 is capable of providing mass storage for the system 600. In general, the storage device 630 can include any non-transitory tangible media configured to store computer readable instructions. In one implementation, the storage device 630 is a computer-readable medium. In various different implementations, the storage device 630 may be a floppy disk device, a hard disk device, an optical disk device, or a tape device.

The input/output device 640 provides input/output operations for the system 600. In some implementations, the input/output device 640 includes a keyboard and/or pointing device. In some implementations, the input/output device 640 includes a display unit for displaying graphical user interfaces.

The features described can be implemented in digital electronic circuitry, or in computer hardware, firmware, or in combinations of them. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Various software architectures can be used for implementing the methods and systems described in this application. For example, a publish/subscribe messaging pattern can be used in implementing the methods and systems described herein. In the case of publish/subscribe messaging, the system includes several hardware and software modules that communicate only via a messaging module. Each module can be configured to perform a specific function. For example, the system can include one or more of a hardware module, a camera module, and a focus module. The hardware module can send commands to the imaging hardware implementing the fast auto-focus, which in turn triggers a camera to acquire images.

A camera module can receive images from the camera and determine camera parameters such as shutter time or focus. Images can also be buffered in the computer's memory before being processed by the camera module. When performing the initial search for the tilt of the slide, the camera module can also send a message interrupting the hardware module when it has seen enough images to determine the proper shutter time or focus.

The system can also include a focus module that can be implemented as software, hardware or a combination of software and hardware. In some implementations, the focus module examines all the frames in a stack and estimates how far the stack is from the ideal or ideal focal distance. The focus module can also be responsible for assigning a focus score to each frame in a stack of images.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Alternatively, the computer can have no keyboard, mouse, or monitor attached and can be controlled remotely by another computer The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 610 carries out instructions related to a computer program. The processor 610 can include hardware such as logic gates, adders, multipliers and counters. The processor 610 can further include a separate arithmetic logic unit (ALU) that performs arithmetic and logical operations.

Other Embodiments

The techniques and systems described herein can be implemented in many ways. Some useful implementations are described above. It is to be understood that the foregoing description is intended to illustrate and not limit the scope of the appended claims. The methods and systems described herein can be used for achieving counting blood cells in other imaging systems, for example, in various medical imaging applications. Other aspects, advantages, and modifications are within the scope of the following claims.

What is claimed is:

1. A method of classifying white blood cells (WBCs) in a biological sample on a substrate, the method comprising:
    acquiring, by an image acquisition device, a plurality of images of a first location on the substrate;
    determining, by a classifier using one or more processing devices, the classifier executing a first classification process, that a given object in the plurality of images is associated with a first classification group selected from a set of multiple WBC classification groups, wherein the first classification process uses a first set of features to select the first classification group for the given object;
    determining, by a classifier using one or more processing devices, the classifier executing a second classification process, that the given object is associated with a second classification group, wherein the second classification process uses a second set of features different from the first set of features;
    in response to determining that the given object is associated with the second classification group, changing a classification of the given object;
    displaying, on a user interface, a representation of the given object and the corresponding classification; and
    removing non-WBC objects from the images prior to classifying the objects, wherein the non-WBC objects include one or more of platelets, clumps, giant platelets, and micromegakaryocytes.

2. The method of claim 1, wherein acquiring the plurality of images includes acquiring the plurality of images using a 50× objective lens.

3. The method of claim 1, comprising determining at least one of a value for a nuclear complexity of neutrophils in the WBC classification groups and a value for an atypicality of lymphocytes in the WBC classification groups.

4. The method of claim 3, comprising displaying at least one of the value for the nuclear complexity and the value for the atypicality on the user interface.

5. The method of claim 1, wherein the objects in the plurality of images are classified using a multi-stage classifier.

6. The method of claim 5, wherein at least one stage of the multi-stage classifier includes a linear discriminant analysis (LDA) based classifier.

7. The method of claim 6, wherein at least another stage of the multi-stage classifier includes a Bayesian classifier.

8. The method of claim 1, wherein the WBC classification groups are based on various stages of WBCs along WBC maturation pathways.

9. The method of claim 1, wherein the corresponding classification includes one of: immature cells, blasts, promonos, and prolymphs.

10. The method of claim 1 comprising excluding rare, damaged, or out-of-focus cells from being classified into the WBC classification groups.

11. The method of claim 1, wherein at least one of the first set of features and the second set of features includes one or more of an area of a WBC, a shape of a WBC, a color of a WBC, and optical density of a WBC, and a texture of a WBC.

12. The method of claim 1, wherein the first classification classifies the objects into groups that include lymphocytes, monocytes, neutrophils, basophils, and eosinophils.

13. A non-transitory computer readable storage device, having encoded thereon computer readable instructions that, when executed by a processor, cause the processor to:
acquire a plurality of images of a biological sample at a first location on a substrate;
remove non-WBC objects from the images prior to classifying the objects, wherein the non-WBC objects include one or more of platelets, clumps, giant platelets, and micromegakaryocytes;
determine, by executing a first classification process using a classifier, that a given object in the plurality of images is associated with a first classification group selected from a set of multiple white blood cell (WBC) classification groups, wherein the first classification process uses a first set of features to select the first classification group for the given object;
determine, by executing a second classification process using a classifier, that the given object is associated with a second classification group, wherein the second classification process uses a second set of features different from the first set of features; and
display on a user interface, a representation of the given object and the corresponding classification.

14. The computer readable storage device of claim 13, comprising instructions for determining at least one of a value for a nuclear complexity of neutrophils in the WBC classification groups and a value for an atypicality of lymphocytes in the WBC classification groups.

15. The computer readable storage device of claim 14, comprising instructions for displaying at least one of the value for the nuclear complexity and the value for the atypicality on the user interface.

16. The computer readable storage device of claim 13, wherein the objects in the plurality of images are classified using a multi-stage classifier.

17. The computer readable storage device of claim 16, wherein at least one stage of the multi-stage classifier includes a linear discriminant analysis (LDA) based classifier, and at least another stage of the multi-stage classifier includes a Bayesian classifier.

18. The computer readable storage device of claim 13, wherein at least one of the first set of features and the second set of features includes one or more of an area of a WBC, a shape of a WBC, a color of a WBC, and optical density of a WBC, and a texture of a WBC.

19. The computer readable storage device of claim 13, wherein a first classification classifies the objects into groups that include lymphocytes, monocytes, neutrophils, basophils, and eosinophils.

20. An imaging system comprising:
an image acquisition device configured to acquire a plurality of images of a first location on a substrate; and
a classifier comprising one or more processing devices, connected to the image acquisition device, the classifier configured to:
determine, by executing a first WBC classification process, that a given object in the plurality of images is associated with a first WBC classification group selected from a set of multiple WBC classification groups, wherein the first WBC classification process uses a first set of features to select the first WBC classification group for the given object;
determine, by executing a second classification process, that the given object is associated with a second WBC classification group, wherein the second WBC classification process uses a second set of features different from the first set of features; and
display on a user interface, a representation of the given object and the corresponding classification,
wherein at least one of the WBC classifications includes a linear discriminant analysis (LDA) classification and at least one of the WBC classifications includes a non-LDA classification.

21. The system of claim 20, wherein at least one of the first set of features and the second set of features includes one or more of an area of a WBC, a shape of a WBC, a color of a WBC, and optical density of a WBC, and a texture of a WBC.

22. The system of claim 20, wherein the first classification classifies the objects into groups that include lymphocytes, monocytes, neutrophils, basophils, and eosinophils.

23. A method for classifying objects in a biological sample on a substrate, the method comprising:
acquiring, by an image acquisition device, one or more images of the biological sample on the substrate;
extracting, by a classifier comprising one or more processing devices, a plurality of features of the objects in the biological sample from the one or more images; and
performing, by the classifier and for each object, at least a first WBC classification and a second WBC classification, the first WBC classification being based on a first feature vector including one or more of the extracted features of the respective object and the second WBC classification being based on a second feature vector different from the first feature vector, each classification subsequent to the first WBC classification including either maintaining a previous WBC classification of the object or changing a previous WBC classification of the object,
wherein at least one of the WBC classifications includes a linear discriminant analysis (LDA) classification and at least one of the WBC classifications includes a non-LDA classification.

24. The method of claim 23, wherein a particular feature vector for a particular WBC classification is composed of more extracted features than an earlier feature vector for an earlier WBC classification.

25. The method of claim 23, wherein the features include one or more of an area of a WBC, a shape of a WBC, a color of a WBC, and optical density of a WBC, and a texture of a WBC.

26. The method of claim 23, wherein the first WBC classification classifies the objects into groups that include lymphocytes, monocytes, neutrophils, basophils, and eosinophils.

27. The method of claim 23, wherein changing previous WBC classification of the object includes either:
classifying the object into a category available during a previous WBC classification, or classifying the object into a category not available during a previous WBC classification.

* * * * *

UNITED STATES PATENT AND TRADEMARK OFFICE
CERTIFICATE OF CORRECTION

PATENT NO. : 9,690,976 B2
APPLICATION NO. : 14/775381
DATED : June 27, 2017
INVENTOR(S) : Michael Zahniser et al.

It is certified that error appears in the above-identified patent and that said Letters Patent is hereby corrected as shown below:

In the Specification

Column 1, Line 6, after "U.S.C." insert --§--.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*